(12) United States Patent
Osorio et al.

(10) Patent No.: US 8,024,032 B1
(45) Date of Patent: Sep. 20, 2011

(54) METHOD AND SYSTEM FOR THE PREDICTION, RAPID DETECTION, WARNING, PREVENTION, OR CONTROL OF CHANGES IN THE BRAIN STATES OF A SUBJECT USING HURST PARAMETER ESTIMATION

(75) Inventors: Ivan Osorio, Leawood, KS (US); Mark G. Frei, Lawrence, KS (US)

(73) Assignee: Flint Hills Scientific LLC, Lawrence, KS (US)

( * ) Notice: Subject to any disclaimer, the term of this patent is extended or adjusted under 35 U.S.C. 154(b) by 1302 days.

(21) Appl. No.: 11/604,407

(22) Filed: Nov. 27, 2006

Related U.S. Application Data

(60) Provisional application No. 60/740,184, filed on Nov. 28, 2005.

(51) Int. Cl.
*A61B 5/04* (2006.01)
(52) U.S. Cl. ........................................ 600/545; 600/544
(58) Field of Classification Search ........... 600/544–545
See application file for complete search history.

(56) References Cited

U.S. PATENT DOCUMENTS

| | | | | |
|---|---|---|---|---|
| 3,696,808 A | * | 10/1972 | Roy et al. | 600/544 |
| 6,144,877 A | * | 11/2000 | DePetrillo | 600/515 |
| 6,549,804 B1 | * | 4/2003 | Osorio et al. | 600/544 |

OTHER PUBLICATIONS

Xiaoli Li, J Polygiannakis, P Kapiris, A Peratzakis, K Eftaxias, X Yao; "Fractal Spectral Analaysis of Pre-epileptic Seizures in Terms of Criticality"; Mar. 8, 2005; Journal of Neural Engineering; 2; pp. 11-16.*
Kannathal Natarajan, Rajendra Acharya U, Fadhilah Alias, Thelma Tiboleng, Sadasivan K Puthusserypady; "Nonlinear Analysis of EEG Signals at Different Mental States"; Mar. 16, 2004; Biomedical Engineering Online 3:7; pp. 1-11.*

* cited by examiner

*Primary Examiner* — Patricia Mallari
*Assistant Examiner* — Michael D'Angelo
(74) *Attorney, Agent, or Firm* — Donald R. Schoonover

(57) ABSTRACT

A system for analyzing signals representative of a subject's brain activity in a signal processor for information indicating the subject's current activity state and for detecting or predicting a change in the activity state. One preferred embodiment uses a method for estimating the Hurst parameter to perform real-time analysis of the electroencephalogram (EEG) or electrocorticogram (ECoG) signals from a subject patient for information indicative of or predictive of a seizure, and to complete the needed analysis at least before clinical seizure onset. The preferred system then performs an output task for prevention or abatement of the seizure, or for recording pertinent data.

11 Claims, 13 Drawing Sheets

Fig. 3 ECoG CONTAINING A SEIZURE EVENT

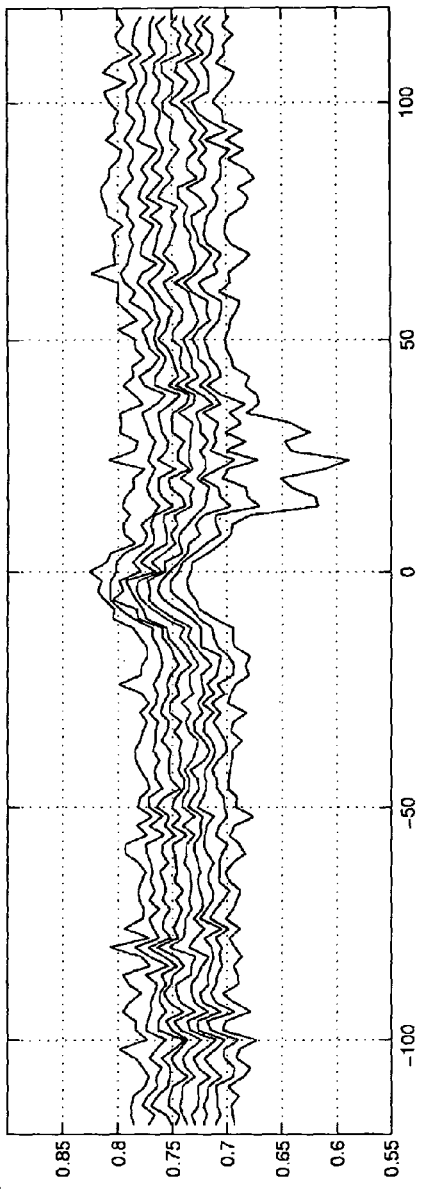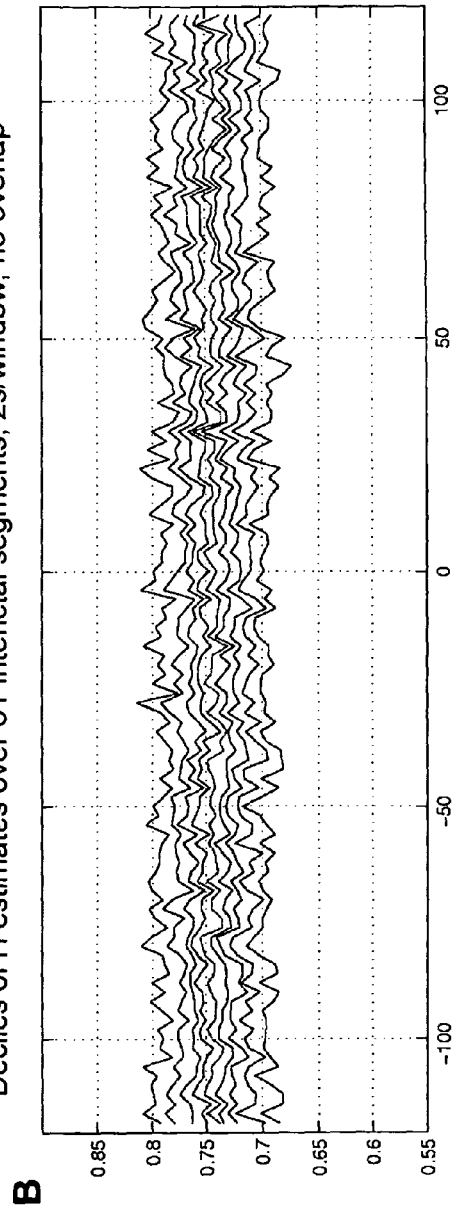
Fig. 6

METHOD AND SYSTEM FOR THE PREDICTION, RAPID DETECTION, WARNING, PREVENTION, OR CONTROL OF CHANGES IN THE BRAIN STATES OF A SUBJECT USING HURST PARAMETER ESTIMATION

CROSS REFERENCE TO RELATED APPLICATIONS

This application claims priority of Provisional Patent Application entitled "Method of Estimating the Hurst Parameter for Detection and Characterization of Brain State Changes", filed Nov. 28, 2005 as Application No. 60/740,184.

BACKGROUND OF THE INVENTION

1. Field of the Invention

The present invention relates to the field of neuroscience for analyzing signals representative of a subject's brain activity including but not limited to signals indicative or predictive of epileptic seizures. More particularly, the invention concerns the automated analysis of brain activity signals to detect an activity state and transitions between states.

2. Brief Glossary of Terms and Useful Definitions

As used herein, certain terms and definitions are used as follows:

ECoG is the abbreviation for electrocorticogram which is a recording of voltage potentials obtained intracranially, e.g., directly from the cortex.

EEG is the abbreviation for electroencephalogram which is a recording of voltage potentials obtained from the scalp and encompasses any recordings outside the dura mater.

EKG is the abbreviation for an electrocardiogram.

EMG is the abbreviation for an electromyogram which is a recording of electrical muscle activity.

EOG is the abbreviation for an electrooculogram which is a recording of eye movements.

Epileptiform discharge and spike are used interchangeably herein to refer to a class of sharply contoured waveforms, usually of relatively large power, and with duration rarely exceeding two hundred milliseconds. Such spikes can form complexes with slow waves, and can occur in singlets, doublets, or in multiplets.

Epileptologist and electroencephalographer are used interchangeably.

False positive detection refers to the case of a system mistakenly detecting a non-seizure signal and classifying it as a seizure.

False negative detection describes the case in which a true seizure goes undetected by a system. Systems that have a low rate of false positive detections are called specific, while those with a low rate of false negative detections are called sensitive.

Ictal Period is the period of time during which a seizure is occurring. Those skilled in the art will appreciate that the term ictal can be applied to phenomena other than seizures.

Interictal Period is the period of time when the patient is not in the state of seizure, or in transition into or out of the seizure state.

Onset of the electrographic component of a seizure is defined by the appearance of a class of signal changes recognized by electroencephalographers as characteristic of a seizure. This analysis requires visual review of signal tracings of varying duration, both before and after the perceived signal changes, using multiple channels of information and clinical correlates. The precise determination of the onset is subject to personal interpretation, and may vary based on the skill and attention level of the reviewer, the quality of data and its display. Onset of the clinical component of a seizure is the earlier of either (1) the time at which the subject is aware that a seizure is beginning (the "aura"), or (2) the time at which an observer recognizes a significant physical or behavioral change typical of a seizure.

Postictal period corresponds to the time period between the end of a seizure and the beginning of the interictal period.

Preictal period corresponds to the time of transition between the interictal and the beginning of the ictal period.

Real-time describes a system with negligible latency between input and output.

State change: Any change in the behavioral, physical or chemical features/signals of a system or of a subject leading from the current to a different state. State changes may be normal or abnormal and endogenous, e.g., onset of sleep, or exogenous, e.g., administration of an anesthetic.

3. Description of the Related Art

Humans and animals have several normal states of behavior such as wakefulness and sleep, as well as multiple sub-states such as attentive wakefulness and REM sleep.

Disorders of the nervous system affect a large segment of the world population. Nervous system disorders include brain disorders that may be neurological or psychiatric, and disorders of the spinal cord, its roots, and peripheral nerves. Examples of such disorders include, but are not limited to, epilepsy, pain, migraine, Parkinson's disease, essential tremor, dystonia, multiple sclerosis (MS), anxiety, panic disorder, obsessive compulsive disorder, depression, bipolar illness, such as narcolepsy, sleep apnea, obesity, and anorexia.

Epilepsy, a disabling disease, affects 1-2% of the American and industrialized world's population, and up to 10% of people in under-developed countries. Electroencephalography is the single most important ancillary test in the investigation of this disease. EEG's are recorded continuously for hours to days in an increasing number of cases with unclear diagnosis or poor response to adequate medical treatment. The amount of EEG data for analysis is extremely large (e.g., sixty-four channels of data at 240 Hz yields 1.3 billion data points/24 hr or 2.6 Gigabytes/day) and consists of complex waveforms with infinite variations.

Visual analysis of these signals remains the "gold standard" but it is impracticable to conduct continuous EEG interpretation as this is the most time-consuming part of any electrodiagnostic test and requires special training and skills which make this procedure expensive and thus of limited access and use. Valuable EEG data is often discarded unexamined. The length of recording is unnecessarily prolonged in a specially equipped hospital suite until patients have several seizures. If the patient is unaware of the seizures, which is a common occurrence, then a nurse or relative must observe and document the presence of these occurrences. As seizures are brief and previously considered unpredictable, the need for continuous observation becomes imperative thereby adding to cost in an inefficient manner.

Present methods of seizure detection are not only expensive, but rely on poorly discriminating methods, increasing the review time and nursing assistance because of the large number of false positive detections, and increasing the length of hospitalization because of false negative detections. Furthermore, these methods often "detect" the seizure well after its onset, when prevention or abatement of the seizure is no longer possible or irrelevant.

The inability to process data in real time has thwarted scientific and clinical development in the fields of epilepsy and electroencephalography. Cardiology has developed into a clinical science largely based on the power of electrocardiography to analyze the heart's electrical activity in a rapid and accurate manner. This has resulted in pacemakers, implanted defibrillators, and other devices which have saved thousands of individuals from premature death. The comparison between cardiology/EKG and epilepsy/EEG must take into account the fact that electrical brain signals are far more complex than signals originating from the heart. This explains in large part the developmental lag between these two disciplines.

Electrical brain signals, because of their spatial and temporal characteristics such as non-stationarity, have resisted accurate real-time automatic manipulation. The prior art methods presently used to characterize these states are severely limited. For example, the prior art consists of a long history of failed attempts to identify changes in EEG during certain behavioral states or tasks and to discern epi-phenomenology from phenomenology, a distinction that would help answer questions of fundamental importance. Other limitations include the inability to determine whether signal spikes are a static marker of epilepsy, or whether they are dynamically related to seizure generation.

Most existing methods of automatic EEG analysis have major limitations which render them virtually useless for widespread, safe and effective clinical applications. These limitations include:

1) Lack of speed: the time it takes most methods to analyze input signals and produce an output which detects or predicts a state change is too lengthy for use in warning, intervention/blockage, or prevention of epileptic seizures and other abnormal brain states;

2) Limited accuracy: prior art methods produce a large number of false positive detections (incorrectly identifying non-seizure activity as a seizure) and false negative detections (failure to identify a true seizure), thereby increasing the technical and financial burden of such activities;

3) Limited adaptability to subject or seizure type;

4) Lack of portability and implantability; and

5) High cost.

Attempts to accurately and reproducibly predict behavioral or biologic signal changes associated with state changes such as seizures have been largely unsuccessful.

There have been, however, important advances in real-time seizure detection in the past fifteen years, most notably in the development of the method and system for seizure detection described in U.S. Pat. No. 5,995,868 to Osorio et al., which is incorporated herein by reference in its entirety. However, the prior art in seizure detection and real-time quantitative analysis of brain state does not utilize the additional, complementary information that can be obtained through determination of long-range dependencies in brain signals, such as those quantified by estimating the Hurst parameter of time series such as with an EEG or ECoG.

PRINCIPAL OBJECTS AND ADVANTAGES OF THE INVENTION

The principal objects and advantages of the present invention include: providing a method and system that enables accurate, automated, real-time detection of seizures, as well as the determination of their site of origin, propagation path and speed through regions of the brain, and their duration and intensity; providing such a method and system that enables the prediction of the onset of the clinical component of seizures; providing such a method and system that enables prediction of the onset of the electrographic component of seizures; providing such a method and system that enables online self-adaptation, or offline adaptation of the aforementioned objects and advantages to each subject patient; providing such a method and system that enables automated application of the aforementioned objects and advantages for diagnosis, quantitative analysis, imaging, warning, enabling of a treatment, and storing of data; providing such a method and system that enables miniaturization to a portable or implantable device; and generally providing such a method and system that is reliable in performance, capable of long-lasting life, and is particularly well adapted for the proposed usages thereof.

Other objects and advantages of this invention will become apparent from the following description taken in conjunction with the accompanying drawings wherein are set forth, by way of illustration and example, certain embodiments of this invention.

SUMMARY OF THE INVENTION

The present invention solves the problems and overcomes the limitations of certain prior art, while providing pioneering advances in the state of the art. The preferred embodiment enables (1) the accurate, automated, real-time detection of seizures, as well as the determination of their site of origin, propagation path and speed through regions of the brain, and their duration and intensity; (2) the prediction of the onset of the clinical component of seizures; (3) the prediction of the onset of the electrographic component of seizures; (4) the online self-adaptation, or offline adaptation of (1-3) to each subject patient; (5) the automated use of (1-3) for diagnosis, quantitative analysis, imaging, warning, enabling of a treatment, and storing of data; and (6) the miniaturization of the system to a portable or implantable device.

The preferred embodiment of the invention uses intracranial or scalp electrodes to obtain signals representative of current brain activity and a signal processor, such as a personal computer or micro-processor, for continuous monitoring and analysis of these signals, and detection of relevant changes predictive of an impending change, such as precursors, as soon as they appear. The output of this analysis is then fed to a device that produces an immediate response (e.g., warning, treatment, or data storage) to the change or predicted change in state.

The Hurst parameter, H, may be estimated on input broadband (e.g., DC-2 KHz) or narrow-band (e.g., 0.5-70 Hz) signals that are a) "raw" or minimally conditioned using commercially available amplifiers, or b) processed via an adaptive analysis of frequency, energy, wave shapes, phase relationships, measures of rhythmicity, "sequency," and temporo-spatial stereotypia, variability, dimension, or complexity of the signal. Noise reduction techniques may be applied as needed.

Real-time seizure detection of the present invention include (i) estimating the Hurst parameter in one or more moving, possibly overlapping, windows/epochs of detected signals; continuously tracking the evolution of H estimates in moving windows and, when the estimate reaches a particular level, immediately issuing a seizure detection; and, optionally, grading and verifying seizures by conducting an analysis of duration, intensity, pattern recognition of spatio-temporal propagation, and postictal seizure signal changes.

The preferred embodiment of the present invention utilizes dispersional analysis (DA), bridge-detrended scaled window variance (bdSWV) and/or re-scaled range (R/S) analysis for detection of seizures and/or seizure precursors and prediction of their electrographic or clinical onset.

The present invention includes applying Hurst parameter estimates and other related measures of temporal dependence to brain signals, such as ECoG, in order to detect and even classify signal changes that may be predictive of an impending brain state change, such as a seizure. Such applications of the present invention detect the occurrence of signal characteristics or patterns, which may be precursors to the clinical and/or electrographic components of seizures, resulting in their prediction.

Methods of the present invention for estimating H can be realized in a signal processor. Real-time detection of (a) seizure precursors and the resulting prediction of the electrographic and clinical seizure components, or (b) the electrographic component and the resulting prediction of the clinical component, enable the institution of safety and therapeutic measures, and initiates or continues the adaptation of the methods. For example, seizure prediction can be used to trigger a device for systemic, intraventricular, or intracerebral administration of a medicament or substance; for electrical, magnetic, or thermal activation or deactivation of a nerve or a region of the subject's brain; for activation or deactivation of physiologic receptors; for ablation of a region of the subject's brain; for activation of a warning or biofeedback device; or for selection of segments of signals for transmission or storage or for annotation of continuously recorded signals and further off-line analysis.

BRIEF DESCRIPTION OF THE DRAWING FIGURES

FIG. 6A shows the evolution of the distribution of H parameter estimates (y-axis, illustrated using ten-percentile divisions) exhibiting an increase approximately fifteen seconds before electrographic seizure onset (time 0 of x-axis) as marked using expert visual analysis.

FIG. 6B shows the evolution of the distribution of H parameter estimates obtained from interictal segments of comparable length.

Figure 10:
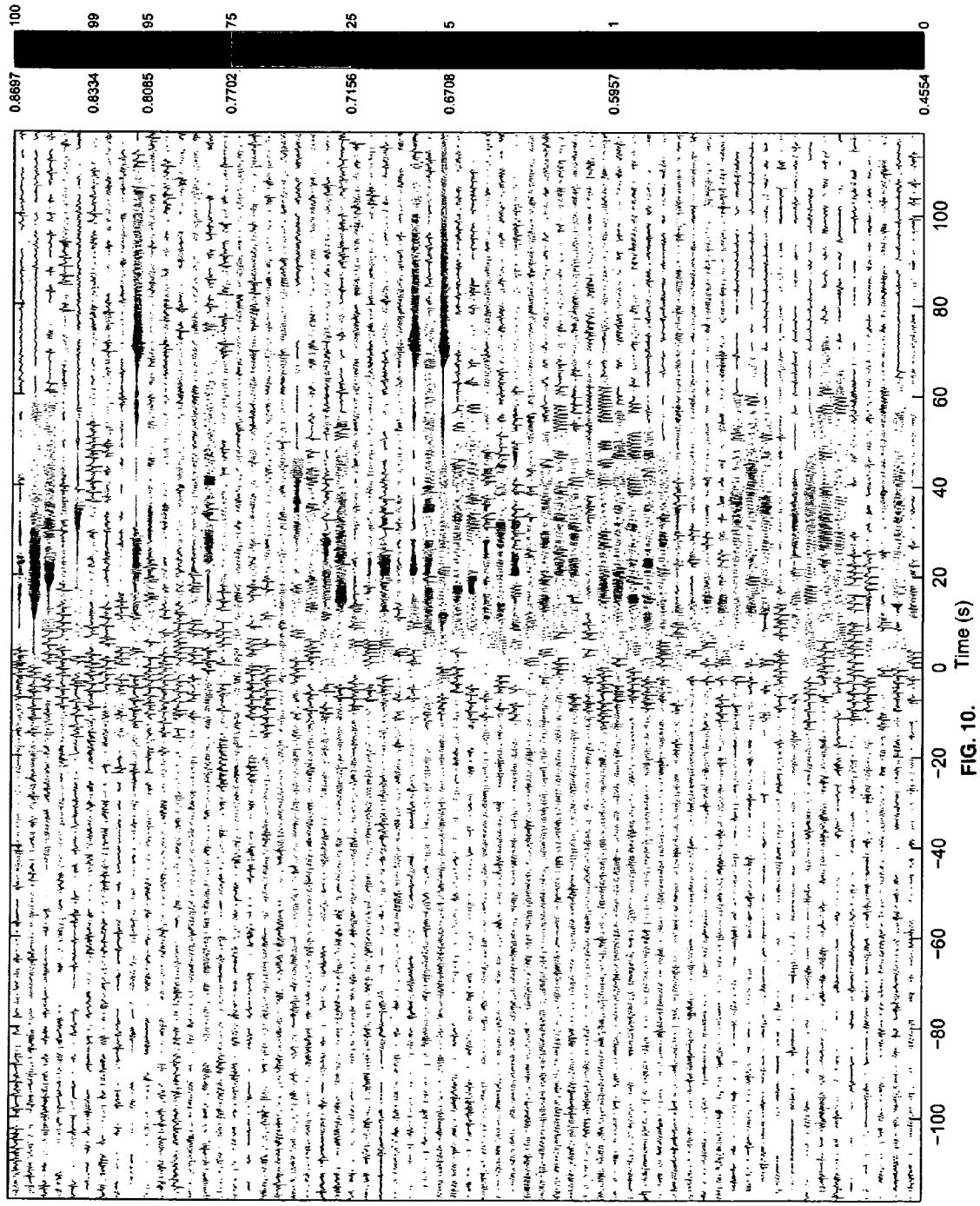

FIG. 10 displays sixty-two ECoG segments, each containing seizure precursors with several of these further evolving to higher frequency electrographic seizures. This illustrates the utility of Hurst parameter estimation for detection, quantification, and classification of different state changes. H estimates are represented by shading changes in the traces, with numerical values indicated in the legend to the right.

Figure 11:
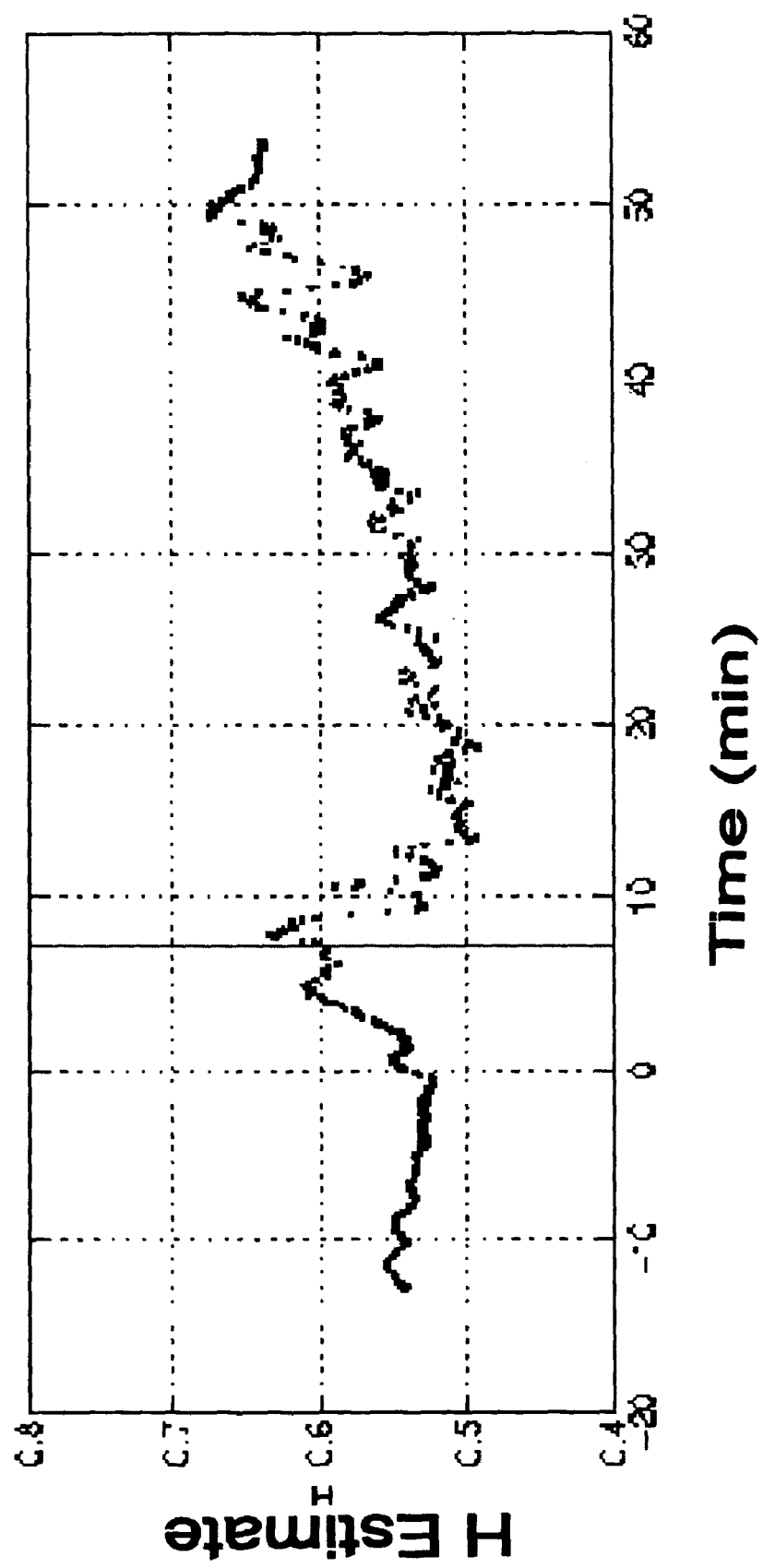

FIG. 11 shows the increase in H estimate obtained from the ECoG of an animal to whom a convulsant substance (3-mercaptopropionic acid) was injected at time 0 (x-axis). The state change (from non-seizure to seizure) manifests with an increase in H values, which precedes the onset of seizures (annotated by a vertical line) by several minutes, thus predicting the state change.

Figure 12:
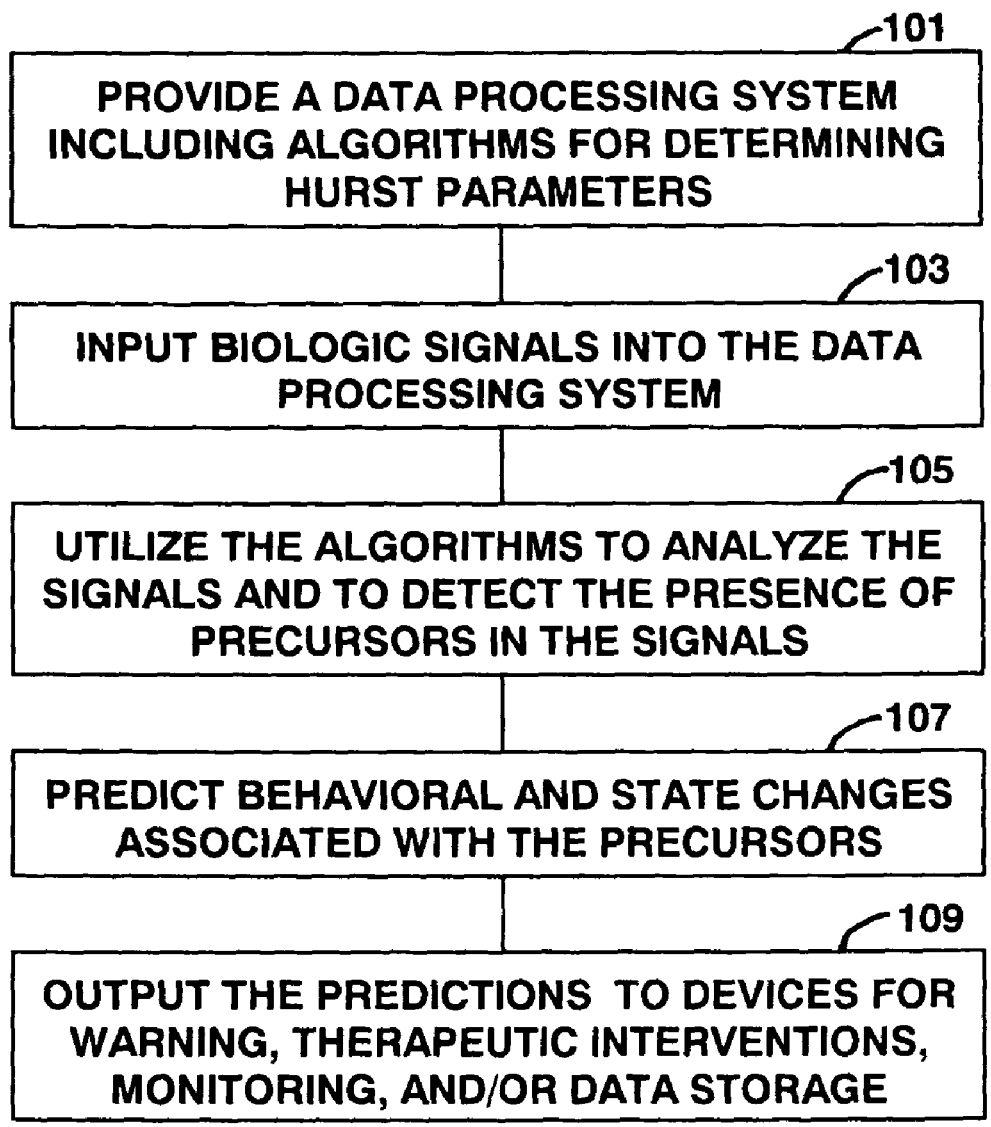
Figure 13:
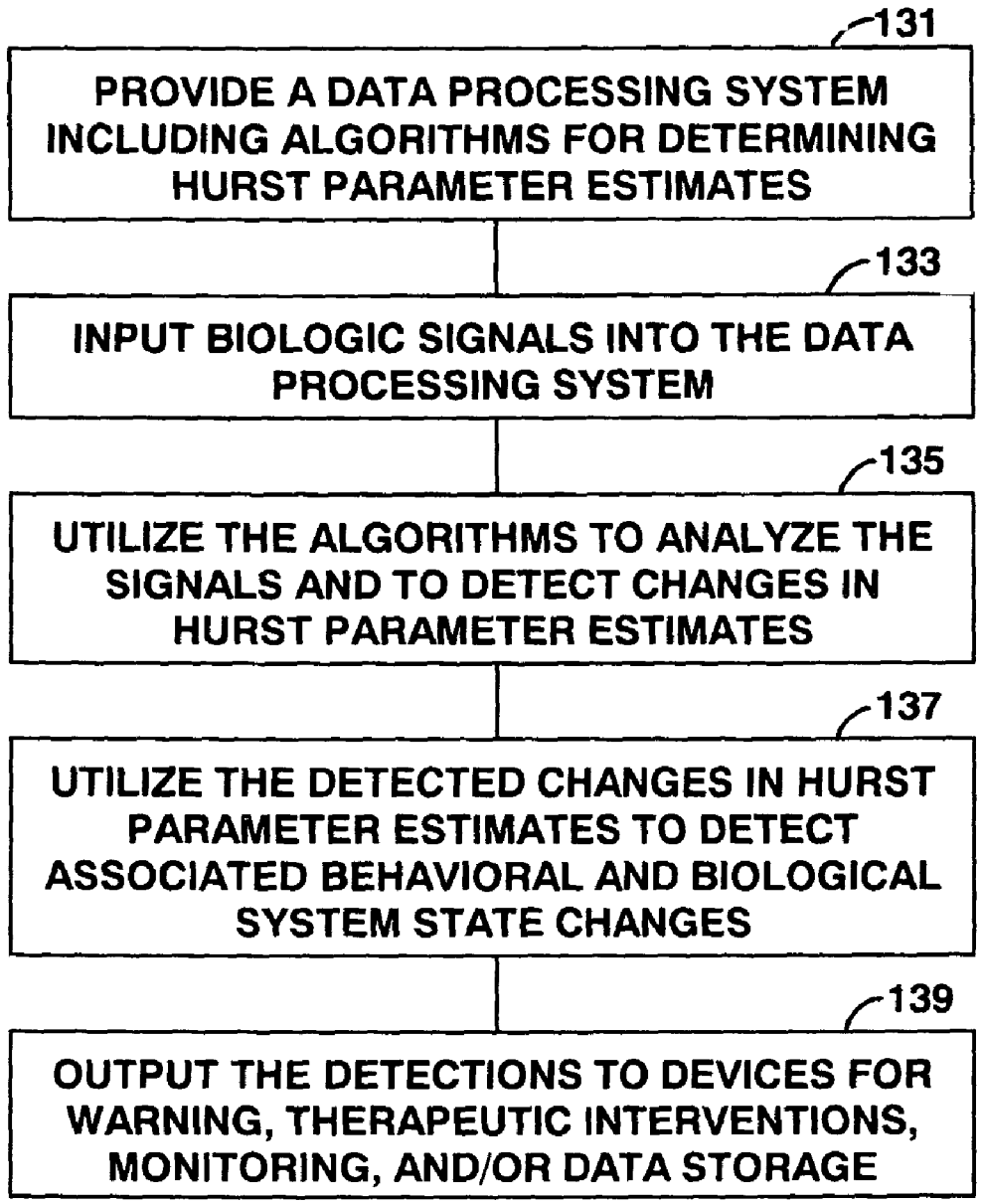

FIGS. 12 and 13 are schematic representations of methods of using the present invention.

DETAILED DESCRIPTION OF THE PREFERRED EMBODIMENTS

As required, embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for claims and as a representative basis for teaching one skilled in the art to variously employ the present invention in virtually any appropriately detailed structure.

The present invention is based on concepts arising from and research in the fields of mathematics, neurology, statistics and engineering which enable the real-time analysis of biologic signals such as those of a electro-encephalogram (EEG) or electrocorticogram (ECoG), or other physical (i.e., temperature), chemical (i.e. neurotransmitter concentrations), or biological signals. In the preferred embodiment, these signals are rapidly, accurately, and automatically analyzed in order to:

1) Detect and announce/warn of the occurrence of a state change, such as an epileptic seizure, in real time (or contemporaneously with the arrival of the signal at the processor/device);

2) Predict state changes such as seizures by detecting precursors to the onset of the electrographic or clinical components of a seizure;

3) Predict behavioral state changes such as those associated with seizures; and

4) Download the detection or prediction outputs to devices for warning, therapeutic interventions, or the storage of data.

The method and system of the present invention enable detection and short-term but worthwhile/useful predictions of electrographic and clinical onset of seizures, making warning, blockage/abatement, and even prevention feasible. Treatment modalities that can be triggered or controlled based on this method and system leads to a significant reduction in seizure frequency and, consequently, to a reduction in the occurrence of injuries and fatalities thereby allowing persons with epilepsy to become productive and to lead normal lives.

The Hurst parameter, sometimes referred to herein as "H", provides information about the presence and type of dependencies in continuous and discrete time series. Hurst parameter estimation is a fundamental component of the invention described herein due to its simplicity and suitability for application to tracking natural phenomena and associated state changes. Of particular value of the present invention is its ability to be implemented into miniature implantable or portable devices due to the relative insensitivity of the Hurst parameter estimates to signal decimation. This characteristic decreases demands on the size and speed of digital signal processors thereby allowing low power implementations. These features translate into more efficient and lower cost devices, as decimated signals and reduced processing enables prolonged battery life and decreases the frequency of surgical procedures required for replacement.

H is also sometimes referred to as a rescaled range statistic, as it may be estimated using the relationship:

$$\frac{R_T}{S_T} \sim T^H \text{ as } T \to \infty$$

where R range, S standard deviation, and T is time. This leads to the Hurst parameter estimator:

$$\hat{H} \sim \log\left(\frac{R_T}{S_T}\right) \Big/ \log(T)$$

Besides this rescaled range estimator, there are several alternative methods to estimate H well known to those skilled in the art including, but not limited to, methods based on: dispersional analysis (DA), bridge-detrended scaled window variance (bdSWV), maximum likelihood estimation (MLE), and Whittle's local estimator.

The following six Tables provide exemplary software fragments written in the MATLAB® scientific programming language, illustrating how various Hurst parameter estimates may be computed from segments of signal/data.

TABLE 1 hurstRS1.m

```
function [H,RS,tau,P]=hurstRS1(x)
%function [H,RS,tau,P]=hurstRS1(x)
%
%This function returns a hurst parameter estimate
%for a scalar time-series x along with RS values
%for windows of size tau (powers of 2 are used)
%and the coefficients of the best fit line
%(P(1)=H, P(2)=proportionality constant, log(C),
%in R (tau)/S(tau) ~ C(tau)^H
x=x(:); N=length(x); N2=floor(log(N)/log(2));
tau=2.^[1:N2]';
RS=zeros(N2,1);              %Preallcoate
for j=1:N2,
    r=[1:tau(j)];
    y=x(r);
    mu=mean(y,1);            %Column mean
    s=std(y,1,1);            %Column std normalized by N
                             (not N-1)
    X=cumsum(y,1)-r'*mu;     %Column computation of X(t,inf)
    RS(j)=(max(X,[ ],1)-min(X,[ ],1))./s;
end;
P=polyfit(log(tau),log(RS),1);
H=P(1);
```

TABLE 2 hurstRS2.m

```
function [h,rs]=hurstRS2(x,n)
% function [h,rs]=hurstRS2(x,n)
%
```

TABLE 2-continued hurstRS2.m

```
% This function estimates the hurst parameter using the
% sample range statistic.
%
if min(size(x))>1,           %x is a matrix
    y=x;
    [n,nwin]=size(y);
else                         %x is a vector
    if nargin<2, n = length(x); x=x(:); end
    y=del_em(x(:),n,1,n);
    nwin=size(y,2);
end
mu=mean(y,1);                %Column mean
s=std (y,1,1);               %Column std normalized by N (not N-1)
X=cumsum(y,1)-[1:n]'*mu;     %Column computation of X(t,inf)
rs=(max(X,[ ],1)-min(X,[ ],1))./s;
h=log(rs)/log(n);
```

TABLE 3 hurst_bdSWV_disp.m

```
%y - matrix of signals, each column corresponding
%to a window of signal to be analyzed
nwin=size(y,2);
%%bdSWV analysis
%Apply Bridge-detrending first
yBD=detrend(y); %Subtract mean and best fit line
w=[1:npts]; w=1-(2*w/(npts+1)-1).^2; w=w(:);
yBD=yBD.*w(:,ones(1,size(yBD,2)));
tau=[2:7 2.^[3:7]]; nt=length(tau); %Define range of tau
values %(window sizes) to analyze over
SDm=zeros(nt,nwin); SDs=SDm; %Preallocate
for j=1:nwin,
    [SDm(:,j), SDs(:,j)]=dispersion(yBD(:,j),tau);
end;
yy=log10(SDs);xx=log10(tau(ones(nwin,1),:)');
xx2=detrend(xx,0);yy2=detrend(yy,0);
for j=1:nwin,
    Hhat_BdSWV(j)=pinv(xx2(:,j)'*xx2(:,j))*(xx2(:,j)'*yy2(:,j));
    %LS fit
end;
%Next use dispersion analysis alone
SDm=zeros(nt,nwin); SDs=SDm; %Preallocate
for j=1:nwin,
    [SDm(:,j), SDs(:,j)]=dispersion(y(:,j),tau);
end;
yy=log10(SDm); xx=log10(tau(ones(nwin,1),:) ' );
xx2=xx-ones(size(xx,1),1)*mean(xx,1);yy2=yy-
ones(size(yy,1), 1)*mean(yy,1);
for j=1:nwin,
    Hhat_disp(j)=1+pinv(xx2(:,j)'*xx2(:,j))*(xx2(:,j)'*yy2(:,j));
    %LS fit
end;
```

TABLE 4 dispersion.m

```
function [SDm, SDs]=dispersion(x,tau)
%function [SDm,SDs]=dispersion(x,tau)
%
%Given an input signal (vector), x,
%this function divides the signal into non-overlapping
%windows of length tau and computes:
%SDm(tau) = the std of local means
%SDs(tau) = the mean of local stds (biased)
%
%Note: If tau is a vector it loops through each tau value
%and produces corresponding vectors of outputs
%
x=x(:);
nt=length(tau);
SDm=zeros(nt,1); SDs=SDm; %Preallocate
```

TABLE 4-continued dispersion.m

```
for i=1:nt,
    y=del_em(x,tau(i),1,tau(i)); %non-overlapping
    m=mean(y,1); s=std(y,1,1);
    SDm(i,1) =std(m,1);
    SDs(i,1)=mean(s);
end;
```

TABLE 5 hurst2mle.m

```
function [h,L]=hurst2mle(x,npts_per_win)
%function [h,L]=hurst2mle(x,npts_per_win)
%
% This function computes a windowed MLE
% of the hurst parameter.
%
x=x(:); %x is a vector
nx=length(x);
if nargin<2, npts_per_win = nx; end;
nwin=floor(nx/npts_per_win);
hlist=[.01:.01:.99]; %Initially we start w/ 99 candidates
r=1:npts_per_win;
h=zeros(nwin,1);L=zeros(length(hlist),nwin); %Preallocate
for iwin=1:nwin,
    ind=(iwin-1)*npts_per_win+r;
    [hh,LL]=h_mle(x(ind),hlist);
    if length(hh)= =1, h(iwin)=hh; else, h(iwin)=NaN; end
    L(1:length(LL),iwin)=LL(:);
end;
```

TABLE 6 h_mle.m

```
function [Hhat,L1]=h_mle(x,hlist)
%function [Hhat,L1]=h_mle(x,hlist)
%
%Inputs:
%
%x = segment of signal (vector)
%hlist = list of h values to optimize over
%
%Outputs:
%
%Hhat = Hurst parameter estimate
%L1 = list of log-likelihood
hlist(hlist>1 | hlist<0)=[ ]; %Restrict estimator candidates
to [0,1]
x=diff(x(:)); %MLE estimator uses pdf of increments
N=size(x,1);
nH=length(hlist);
aimj=[0:N-1]; %Absolute value of i minus j (i.e., |i-j|)
sigma2=1;
L1=zeros(nH,1);
for iH=1:nH,
    H=hlist(iH);
    R=toeplitz( (sigma2/2)*( (aimj+1).^(2*H)-
        2*aimj.^(2*H)+abs(aimj-1).^(2*H)));
    R1=inv(R');
    L1(iH)=(-N/2)*log(x'*R1*x/N) - .5*log(det(R'));
end;
k=find(isfinite(L1));
[L1max,ind]=max(L1(k));
Hhat=hlist(k(ind));
L1=L1-(N/2)*(log(2*pi)+1); %Translate L1to correct log-
likelihood ftn
```

If one wishes to identify a particular state change using a relative change of Hurst parameter with respect to its background/past values (as opposed to an absolute level change), then one may construct, for example, a dimensionless ratio consisting of the running H estimate obtained from the most recent or "foreground" epoch divided by a corresponding longer-term background estimate of H. One skilled in the art will appreciate that time- and state-weighted averaging may be used for the step of constructing such a background as disclosed, for example, in U.S. Pat. No. 5,995,868. More generally, one may also detect and quantify changes in a Hurst parameter estimate for a current epoch of signal, relative to the time- and/or state-weighted distribution of prior or "background" values of these estimates, by analyzing $F_t(H_t)$, where $F_t$ is the time-weighted cumulative distribution function as disclosed in U.S. Pat. No. 6,768,969, incorporated herein by reference in its entirety, and $H_t$ is the Hurst parameter estimate at time t.

H is well suited for detecting the presence and characterizing the nature of long-range dependences (LRD) in natural phenomena, where LRD is a statistical phenomenon describing persistent correlations. This statistical method, originally known as the K parameter and later renamed by Benoit Mandelbrot as the H parameter in honor of its developer, was developed by Edwin Hurst, a British hydrologist. Hurst applied the measure to the study of changes in the levels/discharges of the Nile River and to estimate the size of dams such that, regardless of the amount of rain precipitation, their level would remain relatively constant. That is, they would neither overflow nor dry up.

Development of the present invention revealed that application of H estimators to ECoG time-series containing seizures detects their onset and precursor signal patterns that can indicate an impending seizure. When compared to the background or baseline, these detections appear as changes in the value of H and enable prediction of the electrographic or clinical onset of seizures. While H is highly useful for real-time prediction or detection of brain state changes such as those associated with seizures, it does not necessarily exploit changes in LRD in the ECoG trends, periodicities or other noise that may be consistently found in precursors or seizures that may mimic LRD and cause changes in H.

There are several different estimators for H. The rescaled range statistic ("R/S") is the oldest and perhaps best known. Aggregated variance examines how the variance of a series changes as it is aggregated. The periodogram, or other estimate of the power spectral density of a signal, can be examined and its shape in very low frequency bands can be measured to produce an estimator for H. Wavelets are a method which can be considered as an alternative to the Fourier transform, and the local Whittle estimator examines the behavior of the frequency spectrum near the zero frequency to produce another common H estimator. The first two estimators are in the time domain and the last three in the frequency domain. Although these and other existing estimators for H may disagree when applied to the same data, each of the measures has individual utility for detecting, quantifying, and classifying changes in brain state, and may be used alone or in combination with others to improve reliability and robustness. Other known methods to estimate H include the correlogram method, the use of partial correlations, variance plots, variogram, least squares regression in the spectral domain, Higushi's method, Peng's residuals of regression method, Kettani and Gubner's method of direct estimation from the autocorrelation function, and Abry and Veitch's wavelet-based method. Those skilled in the art appreciate that there are a variety of available methods for Hurst parameter estimation, in addition to those named herein, which may alternatively be utilized within the spirit and scope of the present invention.

Determination of the onset of a seizure by visual analysis, commonly referred to as "the gold standard", is a subjective and empiric process. Additionally, determination of the time of seizure onset depends in part upon the specifications and parameters associated with the recording devices and of the location and type of sensors in regard to the tissue from where the seizure originates. The intensity and degree of spread of the seizure also affect detection.

From a practical standpoint, prediction based on the detection of seizure precursors or the electrographic component itself yields a worthwhile time during which warning and intervention can be instituted to block the onset of either of the components of the seizure. By virtue of their adaptability, the continued application of these prediction methods to a given individual or seizure type may improve the reliability of subsequent predictions, and may lengthen the worthwhile prediction time.

Prediction of seizures may occur during different stages of their temporal evolution:

a) Prediction of the "vibratory" or first state, i.e., the state before the seizure spreads beyond the anatomical or functional boundaries of the "critical epileptogenic mass", which is defined as the smallest mass that triggers subsequent state changes.

b) Prediction of the electrographic component of seizures. This component is mainly defined by temporal continuity of the ictal signal with or without evolution across a frequency spectrum and with propagation outside the critical mass. Prediction of this component can be performed by identifying precursors. Precursors have temporal, spectral, and other characteristics, which distinguish them from the electrographic component.

c) Prediction of the clinical component of seizures. Real-time detection of the electrographic seizure component is akin, for partial or secondarily generalized seizures, to the prediction of the clinical onset as there is a latency between the two components. Precursor detections further lengthen the predictive time of the clinical component.

The Hurst parameter, H, is a useful statistic to investigate for the presence or absence of temporal correlations in natural phenomena. The Hurst parameter has been used to analyze neural membrane channel kinetics, the most fundamental functional operation of the brain. The behavior of membrane channels function, probably exhibits long term correlation, H>0.78 has been reported implying "persistence" for example, and the currents recorded through individual ion channels have self-similar properties, that is, they are fractals and may best be modeled using fractional Brownian motion, "fBm", sometimes denoted by $B^H$. The fractal behavior may extend to the whole neuron as measured simultaneously across many channels. This indicates that brain electrical processes are fractal or self-similar, or at least that useful information may be obtained by treating them as such when analyzing data or signals generated by these processes in the brain. Self-similarity means that for any a>0, $B^H(t)$>0), then $(a^H B^H(t), t>0)$ have the same probability law, where $B^H(t)$, t>0) is a real-valued standard fBm with Hurst parameter H. Long-range dependence means that, for $r(n)=E\{B^H(1)(B^H(n+1)-B^H(n))\}$, the sum over all n of $r(n)=+\infty$.

Figure 1:
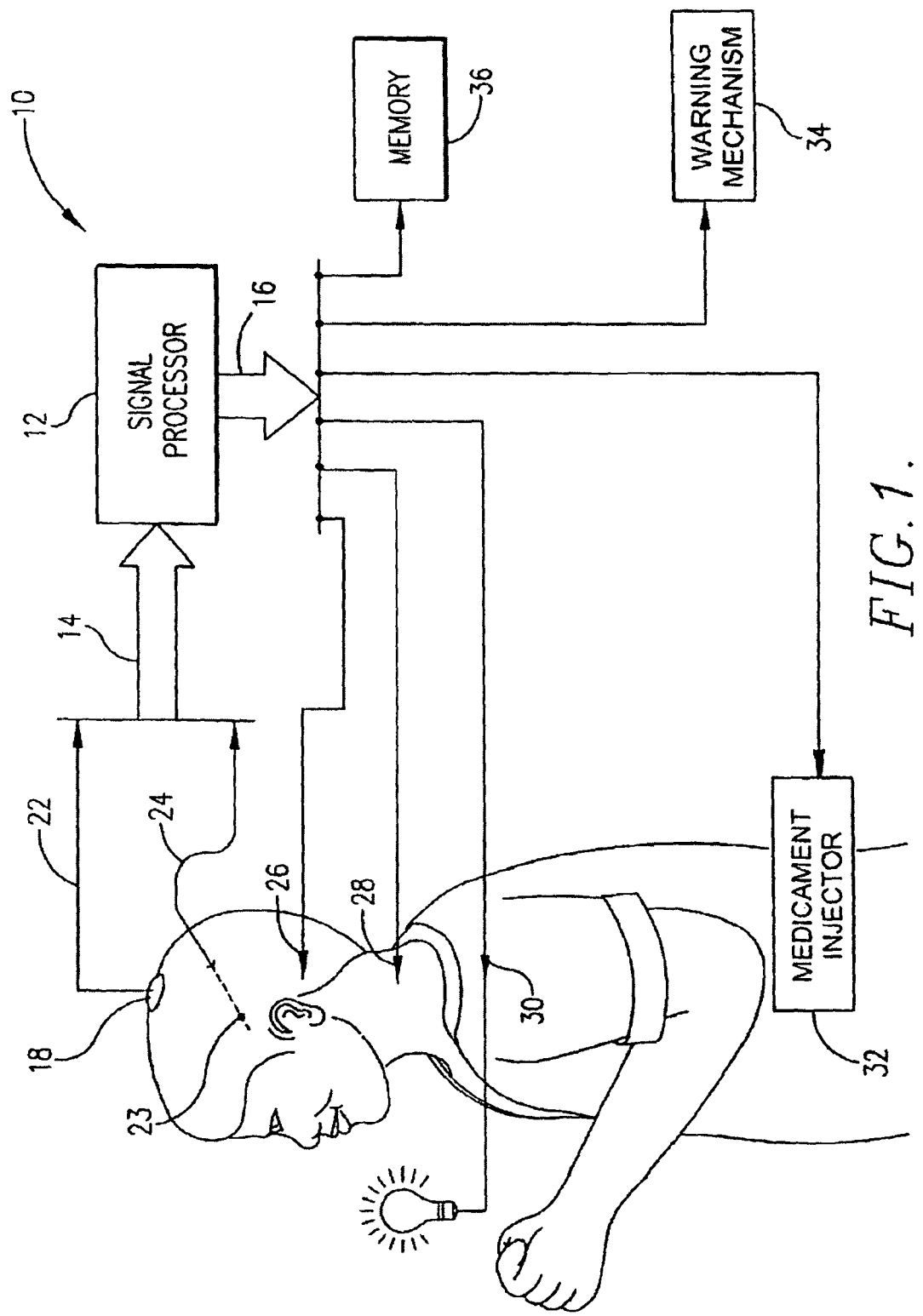
FIG. 1 is a schematic illustration of preferred apparatus of the present invention showing inputs of brain or other biologic system signals of a subject from surface and/or implanted, e.g., intracranial, sensors to a signal processor and various types of outputs.

FIG. 1 illustrates preferred apparatus 10 for receiving and analyzing signals representative of a subject's brain activity and for producing different types of outputs. Apparatus 10 includes signal processor 12, inputs 14, and outputs 16. Signal processor 12 is preferably a computer such as one with capabilities that meet or exceed those of an Intel 486-based computer having 33 MHz clockspeed and 8 MB of RAM. Those skilled in the art will appreciate that an appropriate digital signal processor can be used in place of the preferred computer, as could a custom-designed semi-conductor chip having the requisite capability, preferably configured for implantation or as a portable device. Signal processor 12 could also be an analog processor, or an analog/digital combination.

Inputs 14 include EEG (or other type of scalp) signals obtained from a plurality of scalp sensors 18 transmitted through associated lines 22, or ECoG signals obtained from implanted sensors 23 and transmitted through associated lines 24. The input signals used in the development of the present invention were amplified and converted from analog form to digital form at a rate of 240 Hz with a dynamic range of [−300,300] μV and digital resolution of 0.59 μV (10 bits of precision per datum). Such a procedure provides 144 Kb of data per minute, per channel. Those skilled in the art will appreciate that sampling may be performed at fixed or varying rates (higher or lower than 240 Hz) and precision (with more or less precision than 10 bits), using linear or nonlinear analog to digital conversion, and with constant or varying dynamic range, i.e., adjustable gain. Data acquisition may also be performed using adaptive sampling techniques in which these sampling parameters vary over time and are determined by characteristics of the signal being sampled. Adaptive sampling techniques can be used to selectively enhance relevant signal characteristics and increase signal quality and resolution in certain frequency bands.

Outputs 16 can trigger portable or implanted devices, electrodes 26 which may be intracranial or extracranial, or placed over or around a nerve 28, a medicament injector or pump 32, an audio or LED output, or any other form of warning 34, or auxiliary memory 36 for storing input signals and event data. Implanted electrodes 26 can be used for any form of activation or deactivation, e.g., electrical, thermal, etc., of local or remote brain cells, or for ablation of the epileptogenic tissue. Nerve stimulator 28 is preferably associated with the vagus nerve as such stimulation has been found to abate or prevent a seizure. Physiologic or natural stimulation to receptors, e.g., light to retinal receptors, can prevent or abate seizures and is the function of stimulator 30. Injector 32 is preferably implanted for automated instantaneous release of the appropriate medicament, inclusive of any efficacious substance, for treating, preventing or abating a seizure. Memory 36 is provided to store signal and event data for archival and analysis purposes.

As discussed herein, the analysis performed in signal processor 12 can be customized for a particular patient to improve the detection of brain states and state transitions, and the prediction of changes in brain states. The customization of the signal processing can be based on the information stored in memory 36 via feedback of this information to signal processor 12. For example, this information may be used to monitor efficacy of treatment and to optimize seizure/spike detection and prediction, and therapeutic or safety interventions. Those skilled in the art will also appreciate that memory 36 can be included as an integral part of signal processor 12.

Those skilled in the art will also recognize that changes in cerebral state are highly correlated with changes in level and type of activity of other organ systems, e.g., heart, etc., and, as such, these signals may be useful for detection and prediction or validation of seizures or of other changes in brain state. The following signals (not annotated in FIG. 1) may be used in conjunction with EEG and ECoG signals to further improve performance of the system of the present invention:

1) Non-electrical cerebral signals, global or regional, such as concentrations of glucose, free radicals, metabolic by-products, neuro-transmitters, or other substances, or measurements of intracranial pressure, temperature, blood flow or indices of metabolic activity, etc.;

2) Cardiovascular signals such as heart rate, R-R interval and variability, etc.;

3) Respiratory signals such as tidal volume, peak-to-peak interval, etc.;

4) Electrodermal and other DC potentials;

5) Signals representative of concentrations in the blood or other peripheral tissues of gases, substances, or chemicals such as lactic acid, etc.;

6) Signals representative of the level or type of activity of cranial or peripheral nerves (e.g. frequency and pattern of action potentials, etc.); and/or 7) Signals related to EMG activity, force, direction, and patterns of limb or body movements.

Real Time Seizure Detection.

Successful real-time detection of seizures depends on the ability of any method to rapidly and accurately distinguish the ictal from the non-ictal part of the signal. The preferred embodiment as detailed here is based on a sampling rate of 240 Hz with 10 bits of precision. However, there is a wide range of digitization techniques that may be used, together with the appropriate modifications to the algorithm's parameters within the spirit and scope of the present invention. For example, ECoG may be recorded without using a high-pass filter.

Estimation of the Hurst Parameter

As hereinbefore described, many methods are available for estimating the Hurst parameter, H. The best known estimator is the R/S rescaled range statistic, which is defined according to the following equations:

$$X^*(t) = \Sigma_{s=1}^{t} X(s),$$

$$X^{2*}(t) = \Sigma_{s=1}^{t} X^2(s),$$

$$R(d) = \max_{0 \leq u \leq d} \{X^*(u) - (u/d)X^*(d)\} - \min_{0 \leq u \leq d} \{X^*(u) - (u/d)X^*(d)\},$$

$$S^2(d) = X^{2*}(d)/d - (X^*(d)/d)^2,$$

$$Z(d) = R(d)/S(d)$$

If there exists a real number J such that the limit as d→∞ of $Z(d)/d^J$ converges in distribution to a nondegenerate limit random variable, then the signal $X_t$ is said to have exponent J with constant R/S prefactor and the exponent J is referred to as the Hurst parameter estimate for the signal $X_t$.

Dispersional Analysis.

This statistical approach, originally introduced by Bassingthwaighte, is based on the variability of local averages of the signal over windows of length, τ. It uses standard deviation, SD(τ), of these local averages and repeats the calculation of SD(τ) over many τ values. The estimate of H is then obtained by adding one to the slope of the regression of log [SD(τ)/SD(τ$_0$)] vs. log [τ/τ$_0$], where τ$_0$ is a reference window size.

Bridge Detrended Scaled Windowed Variance.

This statistical approach, introduced by Mandelbrot, divides a signal into windows of size τ and bridge-detrends it, i.e., the line connecting the first and last points in the window is subtracted and then multiplied by a parabolic windowing function. The standard deviation in each of the windows is then computed. The average of the standard deviations is then determined and H is estimated as the slope of the regression of log [SD(τ)/SD(τ$_0$)] vs. log [τ/τ$_0$], where again τ$_0$ is a reference window size.

MLE Estimation.

Another approach is to use parametric models and estimate the parameters of such a model, e.g. by using a maximum likelihood estimator (MLE). One natural model is $$X(t) = \Sigma_{s=1}^{\infty} b(s) X(t-s) + n(s)$$

where {n(s), s=1, 2, ...} are uncorrelated random variables with zero mean and constant variance. By appropriate choice of the coefficients {b(s)} these coefficients have an asymptotic dependence on H. Maximum likelihood estimators have well known consistency properties especially for Gaussian random variables. Whittle has provided an approximate MLE that uses the spectral density that arises from a one step ahead prediction of X. The appropriate MLE can be used with the model to estimate H consistently. Confidence intervals can be obtained for this estimator.

Frequency domain methods can be used to estimate H because Whittle's approximate maximum likelihood estimator (MLE) depends on the spectral density. The integrals of functions of the spectral density in this approximate MLE can be approximated by Riemann sums that can be calculated by the fast Fourier transform to provide an estimate of H. Alternative approaches utilizing wavelets for spectral estimates have also been used and attain the advantages of wavelet analyses over conventional Fourier analysis when the signal under study is nonstationary, as is the case for brain signals. One skilled in the art will appreciate that other alternative approaches may also be utilized for time-frequency-energy analysis of nonstationary signals, such as the method of intrinsic timescale decomposition described in U.S. Pat. No. 7,054,792, which is incorporated herein by reference in its entirety.

A quadratic variation estimate of H can also be used. Consider the quadratic variation $Q_n$ as $$Q_n = \frac{1}{n+1} \sum_{p=0}^{n} (X(p+1) + X(p))^2$$

It follows that $$\log(E(Q_n)) = -2H \log(n) + C,$$

where C is a constant, so it is natural to identify H as the slope of a linear regression of log($Q_n$) with respect to log(n). A simpler version of this approach is $$H_n = \frac{1}{2} \log_2 \left[ \frac{Q_{n/2}}{Q_n} \right].$$

Detecting Changes in Brain State and Precursors to Changes in Brain State Using Hurst Parameter Estimation.

Figure 2:
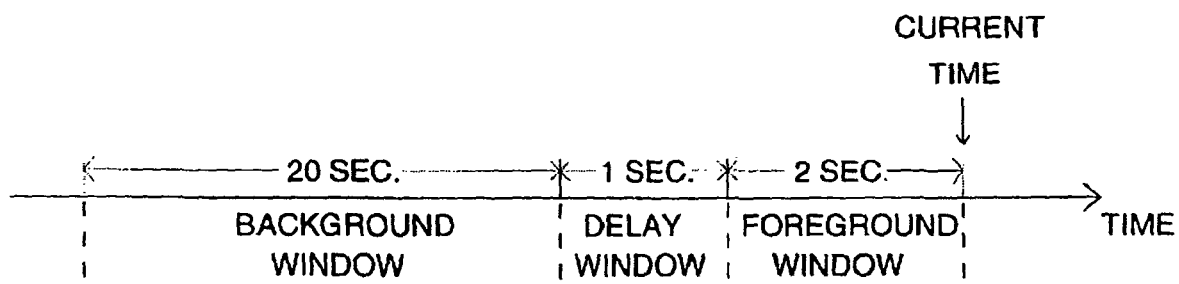
FIG. 2 shows a schematic illustration of the intervals of signal data that may be used for precursor or seizure detection, consisting of current or "foreground" signal activity, e.g., the most recent two seconds, and signal or "background" activity, e.g., a segment of twenty or more seconds in length, delayed one second from the end of the foreground window.

Development of the present invention revealed that estimation of the Hurst parameter in a moving window of data provides a means for detecting changes in brain state, such as those associated with the beginning of an electrographic seizure. Moreover, it has also been determined that the Hurst parameter is sensitive to certain signal changes (referred to herein as "precursors") indicative of probable/impending brain state changes. FIG. 2 shows a schematic illustration of the intervals of signal data that may be used for precursor or seizure detection, consisting of current ("foreground") signal activity (e.g., the most recent two seconds), and signal "background" activity (e.g., a segment of twenty or more seconds in length) delayed one second from the end of the foreground window.

Figure 3:
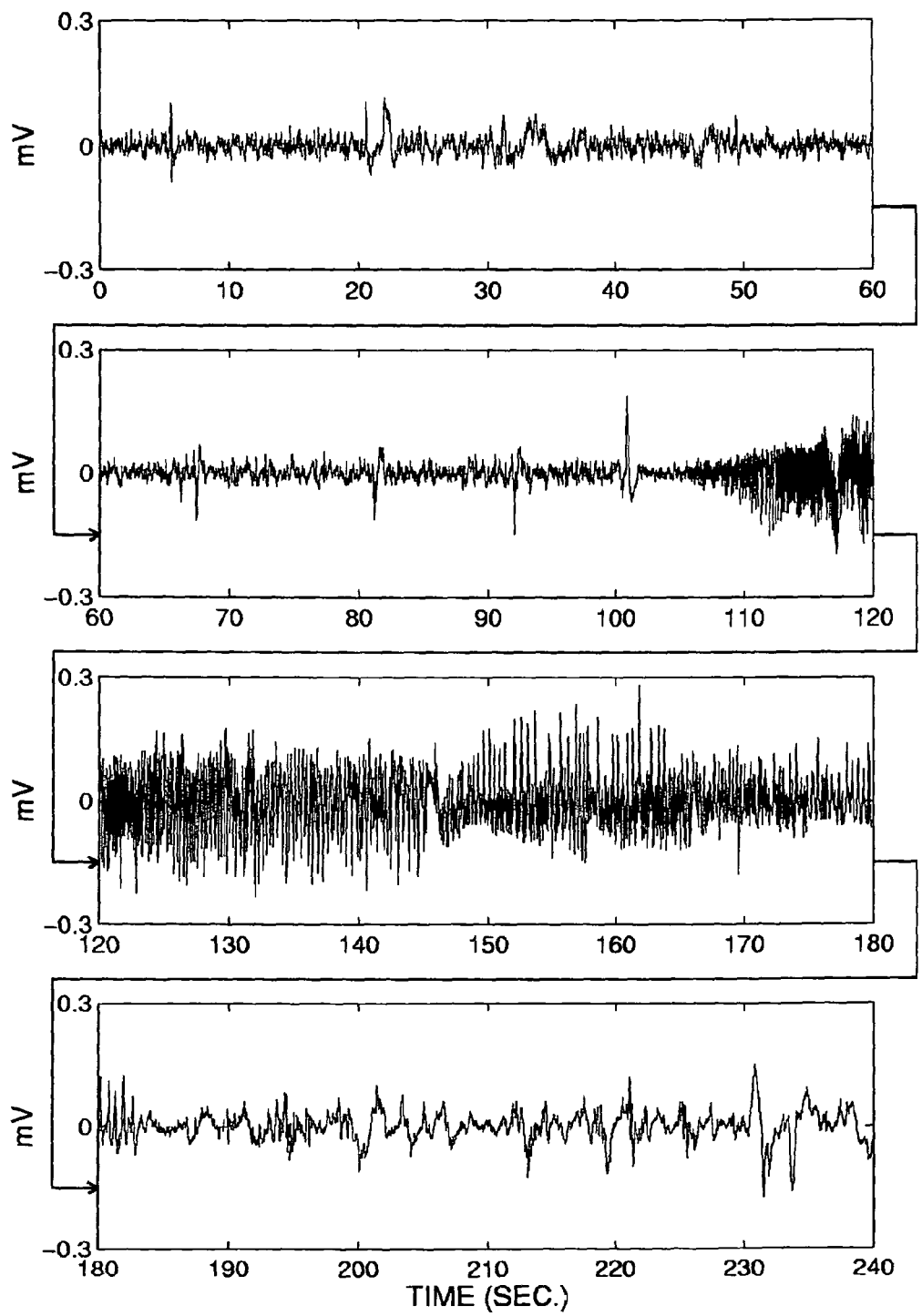
FIG. 3 is a graphical illustration of an ECoG signal containing a seizure used as an input to the apparatus of FIG. 1.
Figure 4:
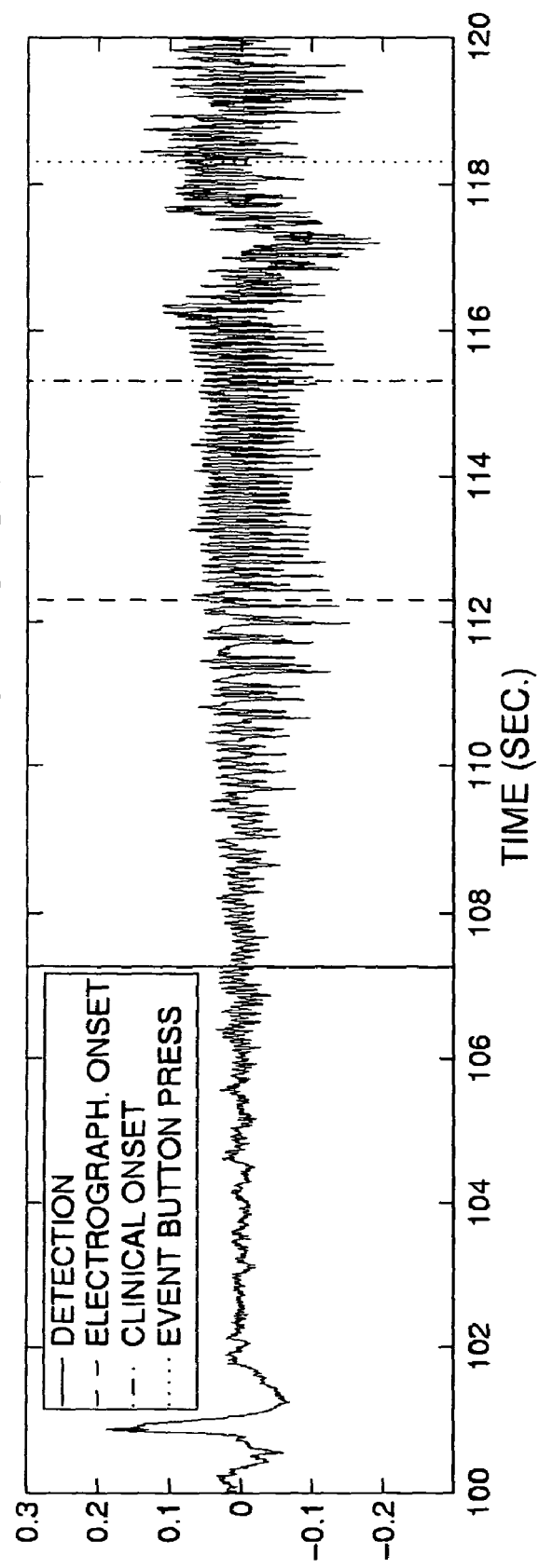
FIG. 4 is a graphical illustration of the part of the ECoG signal shown in FIG. 3 containing the clinical and electrographic seizure onsets and subject activation of an event button.

A preferred embodiment of the present invention uses intracranial or scalp electrodes to obtain signals representative of current brain activity and a signal processor for continuous monitoring and analysis of these signals, in order to detect relevant signal changes as they occur. H may be estimated from an input signal consisting of raw or optionally pre-processed brain signals or other physiologic signals such as those mentioned herein, any of which may exhibit brain state change-related variations in the respective signal's temporal dependencies that may in turn be uncovered via analysis of the corresponding Hurst parameter estimates. In the case of brain potential signals (ECoG or EEG), broad-band (e.g., DC-2 KHz) or narrow-band (e.g., 0.5-70 Hz) signal(s) that are either "raw" or minimally conditioned using commercially available amplifiers may be used. FIG. 3 illustrates a time window of an ECoG signal segment which may be used as an input to the apparatus of FIG. 1. FIG. 4 is a graphical illustration of the part of the ECoG signal shown in FIG. 3 containing the electrographic and clinical seizure onsets and subject activation of an event button, all of which are of interest for detection or prediction purposes.

Figure 5:
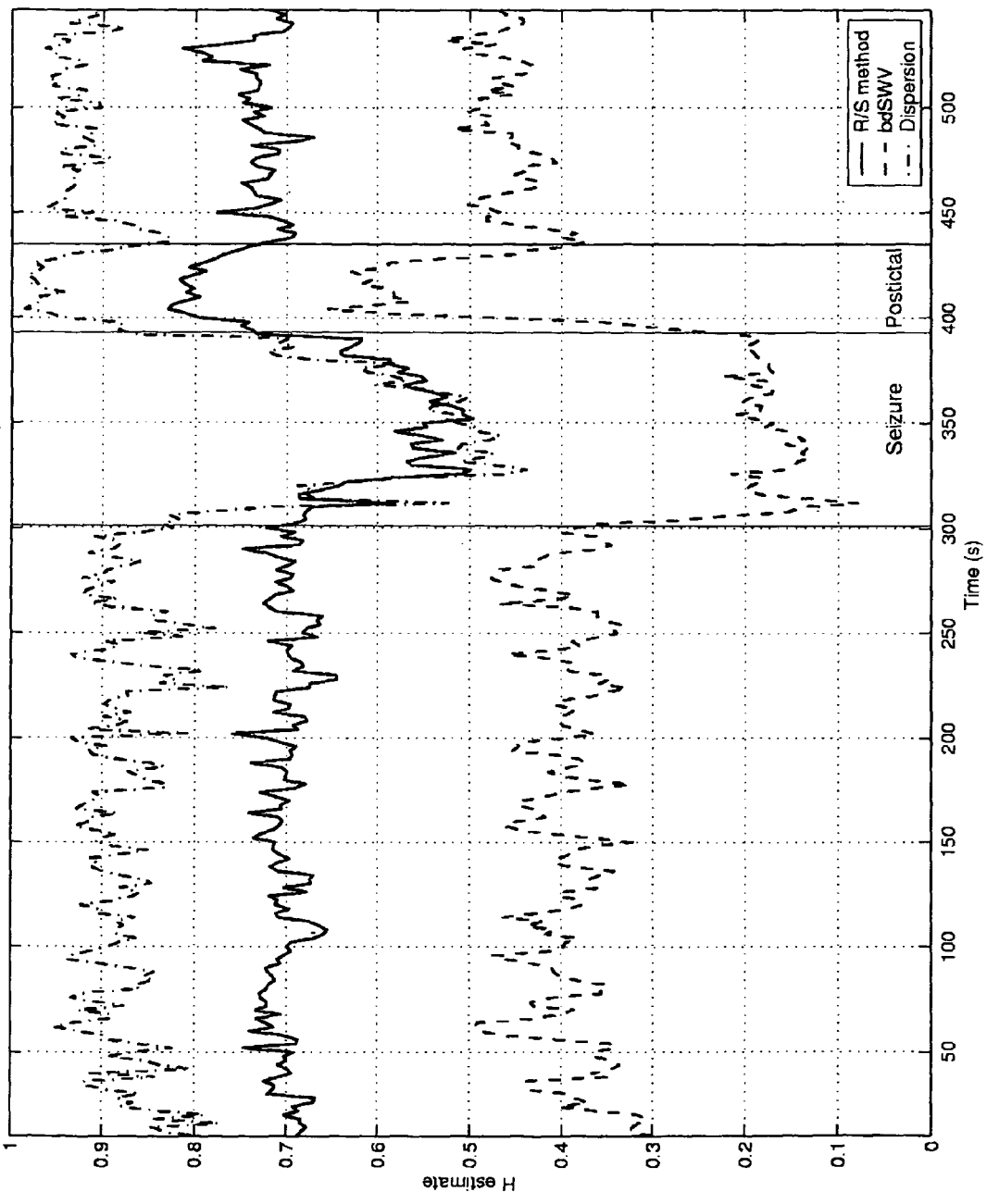
FIG. 5 shows the changes in H parameter estimates (y-axis) obtained using three different methods applied to a foreground window of human ECoG containing a seizure and postictal period (annotated by vertical bars).

One skilled in the art will appreciate that any known methods for Hurst parameter estimation (or a combination thereof), or other means for quantification of signal temporal dependency, can be used to detect relevant changes in brain state, including seizures or their precursors. FIG. 5 illustrates the application of three preferred embodiment methods for H estimation, the R/S, bridge-detrended scaled window variance, and dispersional analysis methods (from top to bottom) to a segment of ECoG containing a seizure. It shows the changes in H parameter estimates (y-axis) applied to a moving foreground window of human ECoG, indicative of the onset and termination of the seizure and postictal periods (annotated by vertical bars). Notice that regardless of the pre-seizure values (which are different for each method), seizure onset is characterized in all of them by the sudden, simultaneous and marked drop in H value, which remains low for the duration of the seizure. H increases rapidly at the end of the seizure, remaining above pre-seizure values for about forty seconds, a period corresponding to the immediate post-seizure state. The return of H to pre-seizure values marks the end of this postictal state and the beginning of the interictal period.

In an alternative embodiment of the present invention, one may analyze optionally preprocessed signals, such as a feature signal derived from the physiologic signals and representative of, for example, an adaptive analysis of frequency, energy, wave shapes, phase relationships, measures of rhythmicity, "sequency," and temporo-spatial stereotypia, variability, dimension, or complexity of the signal. One skilled in the art will appreciate that signal noise reduction and/or signal quality control techniques, such as those disclosed in U.S. Patent Application Publication No. 2004/0138580, which is incorporated herein by reference in its entirety, may be used as desired to ensure good signal quality of the analyzed signal.

Using one or more of the known methods for Hurst parameter estimation, the input signal is analyzed in real time (or offline for retrospective review) and Hurst parameter estimates are computed for one or more signal channels in one or more moving, overlapping, or non-overlapping windows/epochs of the signal of interest. The output of the H estimator is then analyzed to determine whether its most recent value(s) are indicative of a signal change that corresponds to an occurring or impending brain state change. There are a variety of means for making this determination known to one skilled in the art. In one preferred embodiment, the successive values of H estimates are compared to a predetermined threshold level, T, and if the estimate crosses this threshold level (either by uperossing or downcrossing) from its prior "background" levels, a brain state change (e.g., seizure detection) is immediately indicated. As will be appreciated by those skilled in the art, one may also impose a duration constraint on this threshold comparison, so that the detection is not indicated until such time as the Hurst parameter estimates have remained at a particular significant level for at least a minimum designated period of time.

Another alternative embodiment includes the construction of a ratio of the most recent Hurst parameter estimate to a smoothed (e.g., exponentially forgotten) version of the past Hurst parameter estimates and comparison of this ratio value to a threshold level (with or without a duration constraint) in order to determine a detection.

In another embodiment, the system detects and quantifies significant changes in a Hurst parameter estimate for a current epoch of signal, relative to the time- and/or state-weighted distribution of prior "background" values of these estimates, by analyzing $F_t(H_t)$, where $F_t$ is the time-weighted cumulative distribution function as disclosed in U.S. Pat. No. 6,768,969, incorporated by reference herein in its entirety, and $H_t$ is the Hurst parameter estimate at time t. This enables the system to determine changes in $H_t$ that are significant with respect to the entire distribution of past values and to do so in a highly computationally efficient manner. For example, FIG. 6A shows the temporal evolution of the distribution (illustrated using its decile values) of H parameter estimates in moving two-second, non-overlapping windows obtained from sixty-two segments of data each containing seizures. This figure shows an appreciable increase in the distribution of these estimates approximately fifteen seconds before the electrographic seizure onset (at time 0 on the x-axis). For comparison, FIG. 6B shows the evolution of the distribution of H parameter estimates obtained from a similar number of interictal segments of comparable length. It should be noted that these changes in H estimates are seen in all deciles, indicating the sensitivity of the entire distribution of this parameter to relevant signal changes. Notice that seizure precursors or seizures may be associated with increases or decreases in H in a subject specific and consistent way.

The change in Hurst parameter estimates along with their spatio-temporal propagation and nature can be used to determine the duration, intensity, onset location, and pattern of spread of the corresponding brain state changes. This capability mirrors capabilities that are available for other existing state-of-the-art seizure detection methods, such as the method disclosed in U.S. Pat. No. 5,995,868. For example, if the Hurst parameter estimate changes to a level indicative of a presently occurring seizure, and remains at that level for forty-five seconds before changing to a level characteristic of a post-seizure (or "postictal") state for one hundred twenty seconds, then finally recovering back to pre-seizure/interictal levels, this may be used to determine that the duration of the detected seizure was approximately forty-five seconds and may further be used to quantify the duration of the subsequent postictal state.

After a particular brain state change has been detected according to the invention, the output of that analysis is then fed to a device that produces an immediate response to the change or predicted change in state (e.g., warning, automated treatment, data storage, etc.). For example, a seizure detection or prediction can be used to trigger a device for systemic, intraventricular, or intracerebral administration of a medicament or substance, for electrical, magnetic, or thermal activation or deactivation of a nerve or a region of the subject's brain, for activation or deactivation of physiologic receptors, for ablation of a region of the subject's brain, for activation of a warning or biofeedback device, or for selection of segments of signals or other data for transmission or storage (or for annotation of continuously recorded signals) and further off-line analysis.

Robustness and Sensitivity of Hurst Parameter Estimates.

Figure 7:
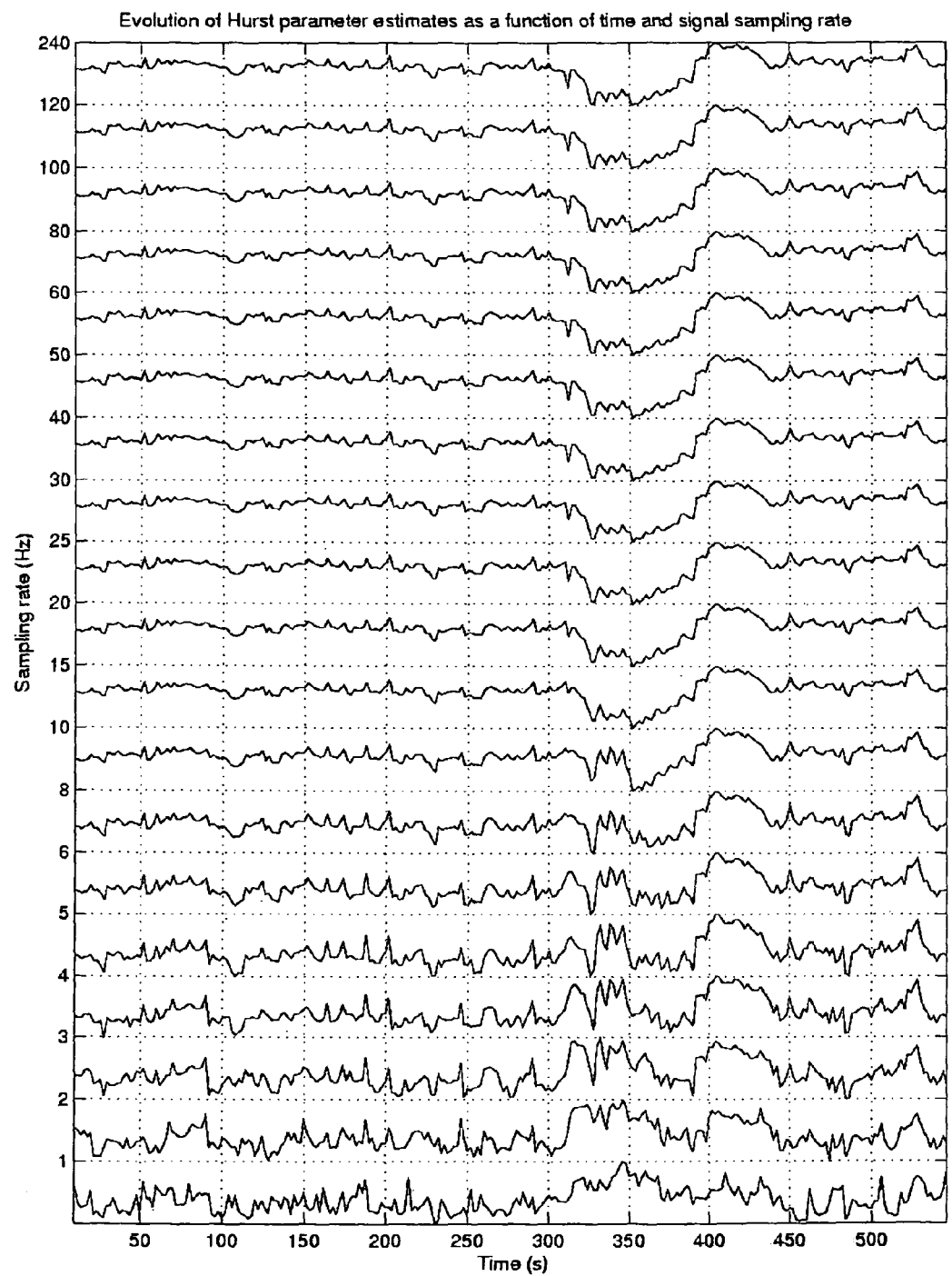
FIG. 7 illustrates the robustness of Hurst parameter estimates as the ECoG signal from which they are obtained is markedly decimated from an original sampling rate of 240 Hz to various lower sampling rates ranging from 120 Hz down to 1 Hz.

A feature of Hurst parameter estimation, which makes it particularly useful in seizure detection or prediction, is its robustness against signal decimation. This is important for low power applications, such as may be required in implantable devices, when the required signal sampling rate and available system memory are significantly limited in comparison with that available for analysis of brain signals with a conventional personal computer or equivalent. FIG. 7 illustrates the robustness of Hurst parameter estimates as the ECoG signal from which they are obtained is markedly decimated from an original sampling rate of 240 Hz to a sampling rate as low as 1 Hz. The figure shows H estimates obtained using a rescaled range Hurst parameter estimator from moving ten-second windows (sliding one second at a time) of ECoG containing a seizure starting at approximately t=300 seconds and ending at approximately t=400 seconds, and the subsequent postictal period until it recovers to baseline values at approximately t=435 seconds. Each trace provides the output obtained when the signal is decimated at the indicated sampling rates (on the y-axis), ranging from 240 Hz down to 1 Hz. The Figure shows that the ability of H estimates to identify the beginning of a seizure remains essentially unaffected by decimation all the way down to the Hz sampling rate. Such decimation would correspond to a factor of sixteen improvement in number of required operations and amount of system memory required to detect the seizure, as compared to the original 240 Hz sampling rate. Moreover, the ability to detect seizure onset is preserved even with sampling rates as low as 1 Hz., even though the direction of change at onset for the lowest sampling rates (<15 Hz.) reverses direction, instead resulting in a brief increase at the onset. This insensitivity to decimation is a very valuable feature for implementation into miniaturized, low-power, implantable devices.

Figure 8:
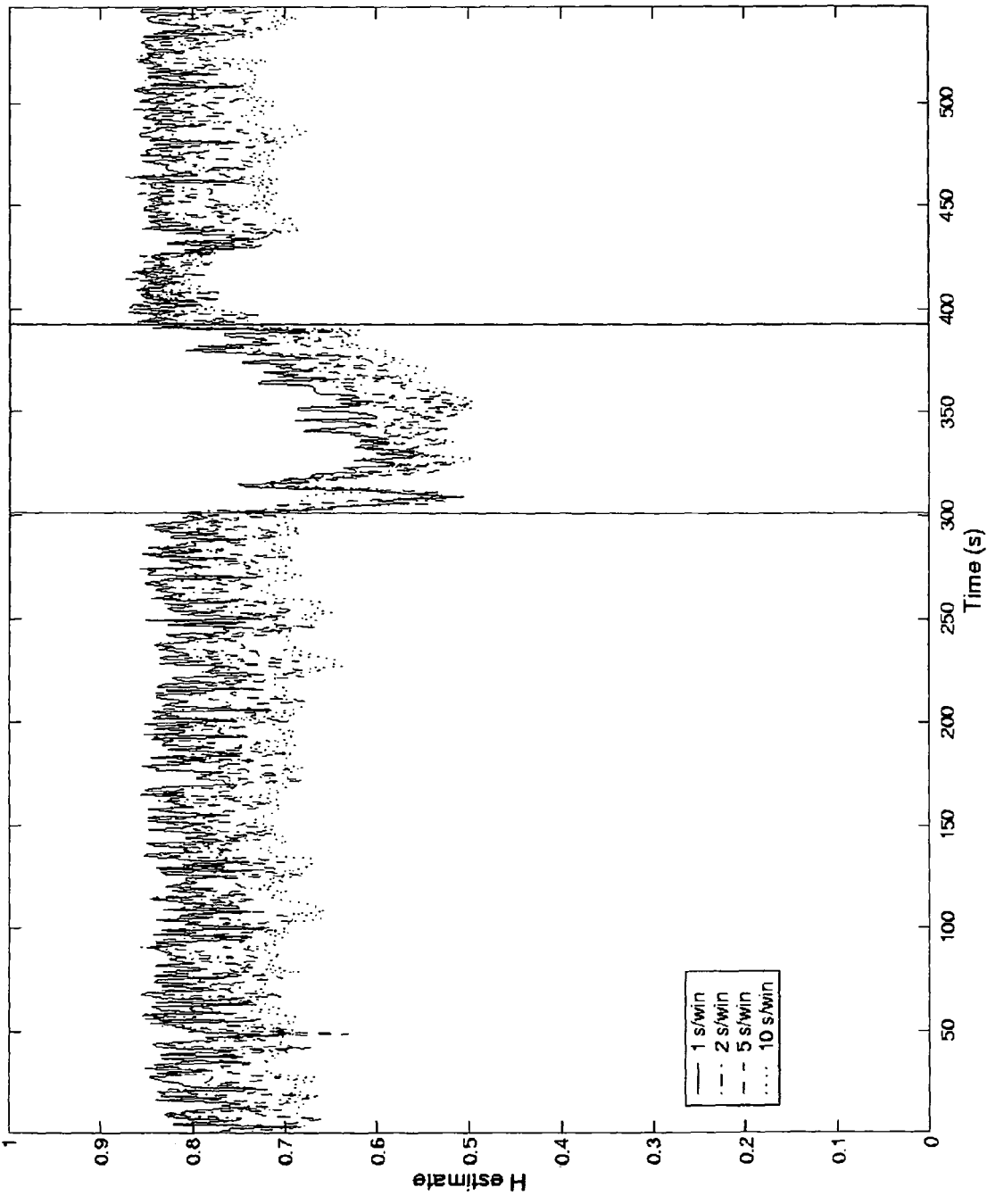
FIG. 8 illustrates the robustness of Hurst parameter estimates obtained from brain signals as window size is varied.

FIG. 8 provides further evidence of the robustness of the invention, in this case showing the ability of the Hurst parameter estimates to detect changes in brain state, over a range of different window sizes from a one-second window to a ten-second window. It should be noted that the changes in H estimates indicative of the onset and end of the seizure occur at the same times regardless of window size.

Figure 9:
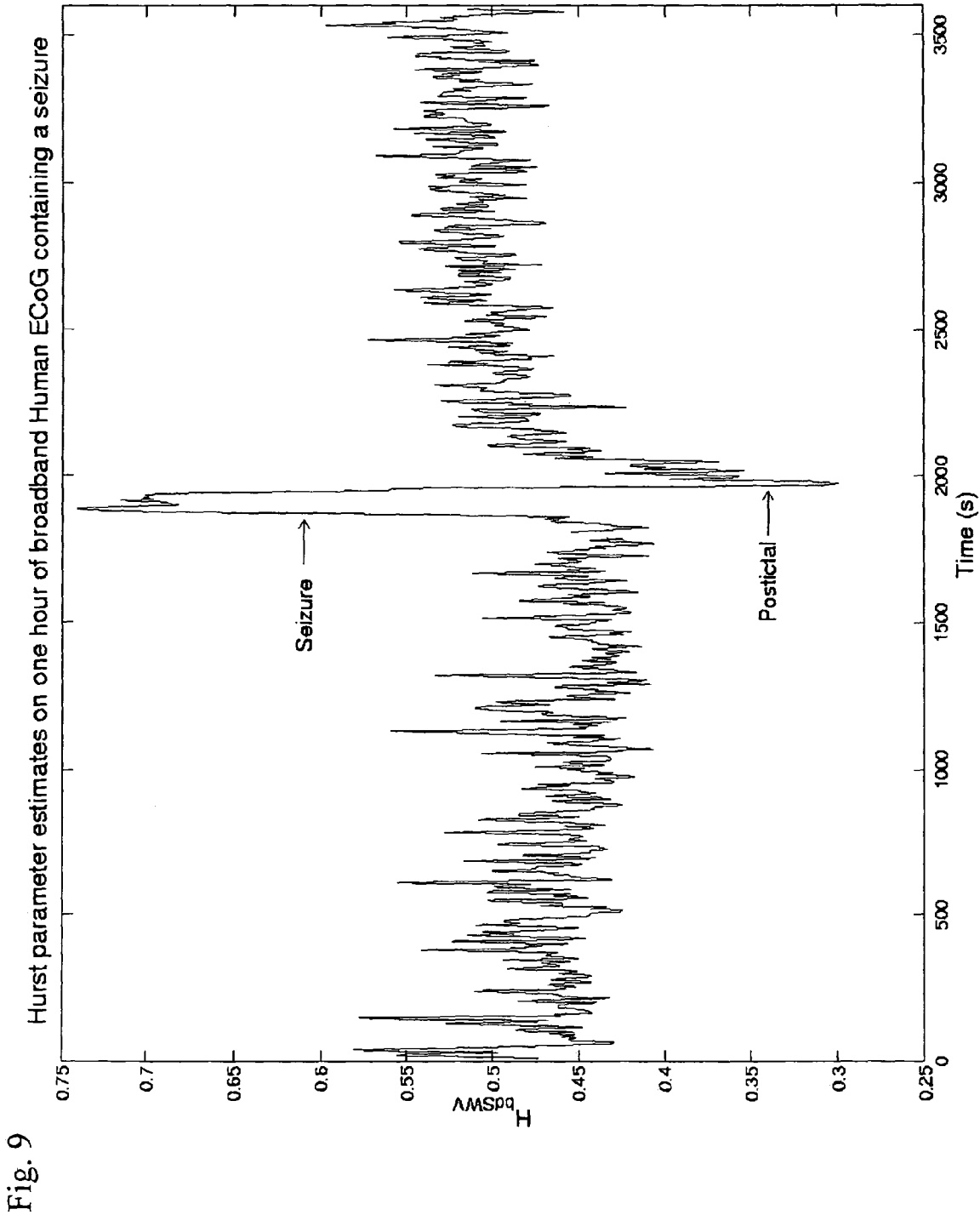
FIG. 9 illustrates the ability of H parameter estimates to detect seizures and postictal states in signals acquired in broadband.

One skilled in the art will appreciate that the information content in the signal varies as a function of filter settings and sampling rates. This is particularly true for electrical potentials recorded from the brain. FIG. 9 shows the result of estimating the Hurst parameter from a one-hour segment containing a seizure and recorded from a human subject using broad-band acquisition parameters (DC-2 kHz filtering, sampled at 20 kHz with 22 bits of precision). A sudden and marked increase in the H estimate signals the onset of the seizure and a sudden drop below baseline corresponding to its termination. The gradual recovery to baseline identifies the duration of the postictal period. This example illustrates the ability of the invention to detect changes over a wide range of acquisition frequency bands. The detection of state changes, such as those corresponding to seizure and postictal periods, may be accompanied by increases or decreases in H parameter estimates, in a stereotypic, subject-specific manner.

The adaptation of the method and system to each individual takes into account, seizure type and location, and changes in the signal(s) over time, making use of any existing preictal, ictal, or postictal "fingerprints" for the subject. The speed of analysis and levels of sensitivity and specificity can also be adjusted to desired levels. This adaptation can be accomplished by selecting the channel or combination of channels used in monitoring, along with the method of Hurst parameter estimation, the lengths of windows and degree of overlap used in monitoring, and the ranges, thresholds, and duration constraints (if any) selected for determination of changes indicative of a desired change in brain state.

FIG. 10 displays sixty-two ECoG segments each containing seizure precursors, with several of these further evolving to higher frequency electrographic seizures. This illustrates the utility of Hurst parameter estimation for detection, quantification, and classification of different state changes and, as specifically exemplified herein, the ability of the invention to predict the electrographic and clinical onsets of seizures. H estimates are represented by shading changes in the traces with numerical values indicated in the legend to the right.

FIG. 11 shows the increase in H estimate obtained from the ECoG of an animal wherein a convulsant substance (3-mercaptopropionic acid) was injected at time 0 (x-axis). The state change (from non-seizure to seizure) manifests with an increase in H values, which precedes the onset of seizures (annotated by a vertical line) by several minutes, thus predicting the state change.

FIG. 12 is a schematic representation of a method employing the present invention, which includes: providing a data processing system including algorithms for determining Hurst parameters, step 101; inputting biologic signals into the data processing system, step 103; utilizing the algorithms to analyze the signals and to detect the presence of precursors in the signals, step 105; predicting behavioral and state changes associated with the precursors, step 107; and outputting the predictions to devices for warning, therapeutic interventions, monitoring, and/or data storage, step 109.

FIG. 13 is a schematic representation of a method employing the present invention, which includes: providing a data processing system including algorithms for determining Hurst parameter estimates, step 131; inputting biologic signals into the data processing system, step 133; utilizing the algorithms to analyze the signals and to detect changes in the Hurst parameter estimates, step 135; utilizing the detected changes in Hurst parameter estimates to detect associated behavioral and biological system state changes, step 137; and outputting the detections to devices for warning, therapeutic interventions, monitoring, and/or data storage, step 139.

It should be appreciated that there are numerous variations of the exemplary embodiments presented herein and that the exemplary embodiments presented are only examples, and are not intended to limit the scope, applicability, or configuration of the invention in any way. The foregoing detailed description will provide those skilled in the art with details and information useful for implementing the invention. It should also be understood that variations of the described embodiments may be implemented without altering the scope of the invention as set forth in the claims hereinbelow.

What is claimed and desired to be covered by Letters Patent is:

1. A method for detecting and quantifying an epileptic seizure in a subject, comprising the steps of:
   (a) receiving signals from a plurality of sensors indicative of brain state of a subject into a processor;
   (b) using the processor to estimate at least one Hurst parameter of the signals in moving time windows and a spatio-temporal propagation of the estimate of the at least one Hurst parameter of the signals in the moving time windows;
   (c) detecting an epileptic seizure by determining if a change in the spatio-temporal propagation of the estimate of the at least one Hurst parameter estimate is indicative of an epileptic seizure in the subject; and (d) determining if at least one feature of the detected epileptic seizure quantifies the seizure, wherein said feature is selected from a set consisting of duration, intensity, onset location, degree of spread, propagation path and speed through regions of the brain being monitored by the plurality of sensors.

2. The method of claim 1, wherein the at least one Hurst parameter is estimated using one of a set consisting of a rescaled range statistic, dispersional analysis, bridge de-trended scaled window variance, correlogram method, the use of partial correlations, variance plots, variogram, least squares progression in the spectral domain, Higushi's method, Peng's residuals of regression method, Kettani and Gubner's method of direct estimation from the autocorrelation function, and Abry and Veitch's wavelet-based method.

3. The method of claim 1, wherein the Hurst parameter is estimated using a broadband signal spanning a range of approximately 0 to 2000 kHz.

4. The method of claim 1, wherein the Hurst parameter is estimated using a signal sampled with a sampling frequency of at least 200 Hz.

5. The method of claim 1, wherein the Hurst parameter is estimated using a signal sampled with a sampling rate below 200 Hz.

6. The method of claim 1, wherein the Hurst parameter is estimated from a narrow-band signal spanning a frequency range from approximately 0.5 Hz to 70 Hz.

7. The method of claim 1, wherein the Hurst parameter is estimated from an unfiltered signal.

8. The method of claim 1, wherein the Hurst parameter is estimated from a preprocessed signal.

9. The method of claim 1, including an additional step of triggering a warning, delivering a therapy, logging an event or storing information or data.

10. A method as described in claim 1, further comprising the step of:

(e) outputting a result of the detecting of an epileptic seizure to at least one device for warning, therapeutic intervention, monitoring, or data storage.

11. A system for detecting and quantifying an epileptic seizure in a subject, comprising:

(a) receiving means configured to receive signals from a plurality of sensors, wherein the signals are indicative of a brain state of a subject;

(b) a processor configured to:
  (1) estimate at least one Hurst parameter of the signals in moving time windows,
  (2) determine a spatio-temporal propagation characteristic of the at least one Hurst parameter estimate,
  (3) detect an epileptic seizure by determining if a change in the spatio-temporal propagation of the at least one Hurst parameter estimate is indicative of an epileptic seizure in the subject, and
  (4) determine at least one feature of the detected epileptic seizure that quantifies the seizure, wherein said feature is selected from a set consisting of duration, intensity, onset location, degree of spread, propagation path and speed through regions of the brain of the subject being monitored by the plurality of sensors; and (c) output means configured to produce an output indicative of the occurrence of an epileptic seizure of the subject.

* * * * *